US008034606B2

(12) United States Patent
Park et al.

(10) Patent No.: US 8,034,606 B2
(45) Date of Patent: Oct. 11, 2011

(54) **ACID TOLERANT *LACTOBACILLUS SAKEI* PROBIO-65 WITH THE ABILITY OF GROWTH SUPPRESSION OF PATHOGENIC MICROORGANISMS AND THE ANTI-ALLERGIC EFFECT**

(75) Inventors: Yong Ha Park, Seoul (KR); In-seon Lee, Suwon-si (KR); Hong-ik Kim, Taejon (KR); Kook-hee Kang, Suwon-si (KR)

(73) Assignee: Probionic Inc., Taejon (KR)

( * ) Notice: Subject to any disclaimer, the term of this patent is extended or adjusted under 35 U.S.C. 154(b) by 903 days.

(21) Appl. No.: 11/883,398

(22) PCT Filed: Jan. 27, 2006

(86) PCT No.: PCT/KR2006/000325
§ 371 (c)(1),
(2), (4) Date: Jan. 24, 2008

(87) PCT Pub. No.: WO2006/080822
PCT Pub. Date: Aug. 3, 2006

(65) Prior Publication Data
US 2009/0214497 A1  Aug. 27, 2009

(30) Foreign Application Priority Data
Jan. 29, 2005 (KR) .................. 10-2005-0008382

(51) Int. Cl.
*C12N 1/20* (2006.01)
(52) U.S. Cl. .................. 435/252.9; 424/93.45
(58) Field of Classification Search .................. None
See application file for complete search history.

(56) References Cited

U.S. PATENT DOCUMENTS
2003/0175305 A1  9/2003  Garner et al.
2004/0214173 A1  10/2004  Berjeaud et al.

FOREIGN PATENT DOCUMENTS
EP  0861905  2/1998

OTHER PUBLICATIONS

Schillinger et al..,Applied and Environmental Microbiology, vol. 55, No. 8, 1989. pp. 1901-1906.*
Eijsink et al. ,Journal of Bacteriology, Apr. 1996, p. 2232-2237.*
Tichaczek et al.,Microbiology (1 994). 140, 361-367.*
Yoon et al, "Reclassification of *Nocardioides simplex* ATCC 13260, ATCC 19565, and ATCC 19566 as *Rhodocuccus erythropolis*," International Journal of Systematic Bacteriology, Jul. 1997, p. 904-907.
English Translation of Abstract: Korean Publication No. KR 1998-78353; Applicant: Korea Institute of Science and Technology; Published Apr. 5, 1999 (Abstract Only) (1 PG).
Sobrino O J et al: "Antibacterial activity of *Lactobacillus sake* isolated from dry fermented sausages" International Journal of Food Microbiology, Elsevier Science Publishers, Amsterdam, NL, vol. 13, No. 1, May 1, 1991, pp. 1-10.
Database WPI Week 199527 Thomson Scientific, London, GB; An 1995-206779 XP002521163 -& WO 95/14485 A (null) Jun. 1, 1995 C:\EPOPROGS\sea\.\..\..\epodata\sea\eplogf\internal.log.
Park Chun Wook et al: "New functional 1-8 probiotic *Lactobacillus sakei* probio 65 alleviates atopic symptoms in the mouse" Journal of Medicinal Food, vol. 11, No. 3, Sep. 2008, pp. 405-412.

* cited by examiner

*Primary Examiner* — Irene Marx
(74) *Attorney, Agent, or Firm* — Casimir Jones, S.C.

(57) ABSTRACT

Disclosed are a novel tactic acid bacterium, *Lactobacillus sakei* Probio-65, and the use thereof. The *L. sakei* Probio-65 strain has acid tolerance, bile acid tolerance and antibiotic resistance, inhibits the growth of harmful pathogenic microorganisms in the body and the intestine of animals, and has immunuenhancing activity. In particular, the novel strain inhibits the growth of *Staphylocccus aureus*, which is known to be a factor aggravating atopic dermatitis. Thus, the novel strain is useful for preventing or treating atopic dermatitis and allergy-related disorders. Also, the novel strain stabilizes intestinal microflors by inhibiting the abnormal proliferation of harmful microorganisms in the intestine. The *L. sakei* Probio-65 strain or a culture thereof is useful in pharmaceutical, feed, food, and cosmetic compositions.

1 Claim, 3 Drawing Sheets ic acid produced by lactic acid bacteria has therapeutic effects on diarrhea, and bacteriocin present in some lactic acid bacteria has antimicrobial effects.

ACID TOLERANT *LACTOBACILLUS SAKEI* PROBIO-65 WITH THE ABILITY OF GROWTH SUPPRESSION OF PATHOGENIC MICROORGANISMS AND THE ANTI-ALLERGIC EFFECT

TECHNICAL FIELD

The present invention relates to a novel lactic acid bacterium, *Lactobacillus sakei* Probio-65, and the use thereof.

More particularly, the present invention relates to *Lactobacillus sakei* Probio-65, which has acid tolerance, bile acid tolerance and antibiotic resistance, as well as effectively inhibiting the growth of harmful pathogenic microorganisms and having anti-allergic activity, and pharmaceutical, feed, food, and cosmetic compositions, comprising the microorganism or a culture thereof.

BACKGROUND ART

Atopic dermatitis is an inflammatory skin disease, which is characterized by severe itching and eczematous skin lesions and mainly affects infants and children. In particular, in chronic instances, atopic dermatitis often recurs in the winter. Such developed atopic dermatitis often progresses to bronchial asthma or allergic rhinitis, and it occasionally recurs in adults. The severe itching afflicting atopic dermatitis patients may cause a reduction in ability to adapt new environments, physical activity and work efficiency, insomnia, and emotional disturbance. Eczematous skin lesions accompanied by pigmentation bring about an ugly appearance, which may hinder normal personal relationships and social activity. Also, dry and irritant-sensitive skin often develops irritant contact dermatitis, which may be a limiting factor in looking for a job. In recent years, the incidence of atopic dermatitis is increasing worldwide, and is also increasing in South Korea along with the rapid increase in allergic diseases. According to a survey conducted by the Korean Academy of Allergy and Respiratory Disease with a total of 43,045 elementary school and junior high school students nationwide in 2000, 24.9% of elementary school students and 12.8% of junior high school students were diagnosed as having atopic dermatitis. In South Korea, the incidence of atopic dermatitis has increased by 50% for the past ten years, this increase rate being much higher among older people. That is, atopic dermatitis was observed at a high incidence of about 17% in adults.

Atopic dermatitis is thought to result from an interaction between genetic, immunological, and environmental factors. The genetic factors include atopy-associated genes, which are mostly immunological genes. The atopy-associated genes identified so far include human leukocyte antigen (HLA) molecules and chromosome 6p, T cell receptor (TCR) and chromosome 7p, IgE high-affinity receptor (FcεRI-β) and chromosome 11q, and IL-4 and chromosome 5q. The environmental factors may be household mites, household dust, fungi, harmful substances, such as formalin and methylbenzene, released from building materials or paint into the air, or chemical substances used as food additives or food itself.

As an environmental factor, *Staphylococcus aureus* is a secondary cause of the worsening of apotic dermatitis. *S. aureus* colonization is found in 80-100% of the eczematous lesions of patients with atopic dermatitis. This is much higher than its occurrence at about 5-30% in the healthy skin. *S. aureus* makes atopic dermatitis skin lesions worse, for example, by increasing impetigo, and spreads to other individuals, thereby making them susceptible to infections leading to atopic dermatitis. There has been evidence supporting the notion that exotoxins produced by *S. aureus* act as superantigens in the worsening of atopic dermatitis. Such exotoxins include staphylococcal enterotoxins A-D (SEA-D) and toxic shock syndrome toxin-1 (TSST-1), which increase IgE production about eight times.

Atopic dermatitis patients have commonly been treated using antibiotic therapy, antihistamine therapy, steroid therapy, immunological therapy, and the like. Antibiotic therapy is used to block secondary microbial infections with such as *S. aureus*, as described above. However, antibiotic therapy is problematic because antibiotics are administered unsuitably, and antibiotic-resistant strains of *S. aureus* have recently tended to increase. Major antibiotic-resistant strains worldwide include methicillin-resistant *Staphylococcus aureus* (MRSA), and methicillin-resistant-coagulase-negative *Staphylococcus aureus* (MRCNS). Thus, owing to a worldwide tendency to avoid the abuse of antibiotics, side effects of the antibiotics, and the emergence of resistant strains, there is an urgent need for the development of materials substituting for antibiotics and other drugs.

In addition, a variety of microorganisms, known as intestinal microflora, inhabit the intestine of humans and animals. Some microorganisms, such as lactic acid bacteria, are known to be beneficial to host animals, and other microorganisms, such as *E. coli*, *Salmonella* or *Staphylococcus*, have direct or potential harmful effects on hosts. In humans and animals, increased stress, infection with harmful bacteria and changes in the external environment may destroy the balance of intestinal microflora, leading to the rapid growth of harmful microorganisms. In this case, the health states of host animals are worsened. Such a change in intestinal microflora brings about allergic diseases. As described above, therapy with antibiotic administration for a long period of time imparts antibiotic resistance to the harmful microorganisms, thereby making effective treatment impossible.

As an alternative regimen of such antibiotic therapy, probiotics are currently receiving increasing interest. Probiotics are prepared by isolating beneficial microorganisms inhabiting the intestine of humans or animals and formulating them into a dosage form. Aerobic bacteria, anaerobic bacteria, lactic acid bacteria, and yeasts are used, lactic acid bacteria being mainly used. Lactic acid bacteria have various applications in traditional food fermentation and processing. Lactic acid bacteria have also been known to be safe for a long time, and some strains thereof are listed as "generally recognized as safe (GRAS)" by the American FDA. Thus, probiotics prepared with lactic acid bacteria have various advantages as follows. They do not have side effects caused by the abuse of antibiotics, and maintain stable intestinal flora by inhibiting the abnormal fermentation of harmful intestinal microorganisms. Also, probiotics reduce diseases caused by infection with harmful microorganisms, and prevent or treat allergic diseases by enhancing the immune system. Among lactic acid bacteria, *Lactobacillus* species, which are lactobacilli carrying out homolactic or heterolactic fermentation, are naturally found in the intestinal tract of animals, including humans, and during the fermentation of dairy products and vegetables. *Lactobacillus* species create an acidic environment in the intestine, which helps inhibit the proliferation of harmful bacteria, such as *E. coli* or *Clostridium*, relieve diarrhea and constipation, and, as well, offer other health benefits, including enhancement of the immune system, vitamin synthesis, protection against cancer, and serum cholesterol level reduction. Acidophillin, produced by lactobacilli, has been found to inhibit the growth of harmful microorganisms, such as *Shigella*, *Salmonella*, *Staphylococcus*, and *E. coli*. Also, acidophillin functions to stop diarrhea by inhibiting the proliferation of diarrhea-causing bacteria and normalizing intestinal flora.

Recently, research has been actively conducted to develop probiotics and animal feed using the aforementioned features of *Lactobacillus* species. Bacterial diarrhea causes reduced body weight gain and death of domestic and farm animals. To prevent the bacterial diarrhea and increase the productivity of farm animals, animal feed has been typically supplemented with antibiotic substances. However, due to the emergence of antibiotic-resistant bacteria and residual antibiotics in livestock products, current regulations in many countries restrict the use of antibiotics in animal feed, and organic feeding programs have been emphasized. At present, the use of probiotics as a substitute method for the use of antibiotics is strongly recommended. European Pat. No. 0861905 discloses a novel *Lactobacillus* sp. strain, and a pharmaceutical composition and a dairy product for treating gastrointestinal disorders, comprising the novel strain. International Pat. Publication No. WO99/29833 discloses *Lactobacillus paracasei*, which is a bacterial strain useful as probiotics in food and naturopathic medicines. Korean Pat. Laid-open Publication No. 1998-78353 discloses a novel acid-tolerant microorganism belonging to the genus *Lactobacillus*, having inhibitory activity on harmful microorganisms, and a probiotic for livestock comprising the novel microorganism.

DISCLOSURE OF THE INVENTION

The present inventors screened for a probiotic microorganism, which is able to more effectively inhibit harmful microorganisms than do conventional probiotics and has acid tolerance and bile acid tolerance. As a result, the present inventors isolated and identified *Lactobacillus sakei* Probio-65, which is able to effectively inhibit the proliferation of *Staphylococcus aureus*, which is a factor aggravating atopic disorders, from Kimchi. The present microorganism was found to be nontoxic to humans and animals and thus very safe, exhibited resistance to various antibiotics, and showed effects of inhibiting the growth of a broad spectrum of pathogenic microorganisms, including the pathogenic bacterium *Staphylococcus aureus*, regulating abnormal intestinal fermentation, and enhancing the immune system. Thus, the present microorganism is potentially useful in pharmaceutical, feed, food, and cosmetic compositions.

It is therefore an object of the present invention to provide a novel microorganism, *Lactobacillus sakei* Probio-65.

It is another object of the present invention to provide a composition for inhibiting the growth of harmful pathogenic microorganisms, comprising the novel microorganism or a culture thereof.

It is a further object of the present invention to provide a composition for preventing and treating abnormal fermentation in the intestine, comprising the novel microorganism or a culture thereof.

It is yet another object of the present invention to provide a composition for preventing and treating allergy-associated disorders, comprising the novel microorganism or a culture thereof.

It is still another object of the present invention to provide a feed composition comprising the novel microorganism or a culture thereof.

It is still another object of the present invention to provide a food composition comprising the novel microorganism or a culture thereof.

It is still another object of the present invention to provide a cosmetic composition comprising a culture of the novel microorganism.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
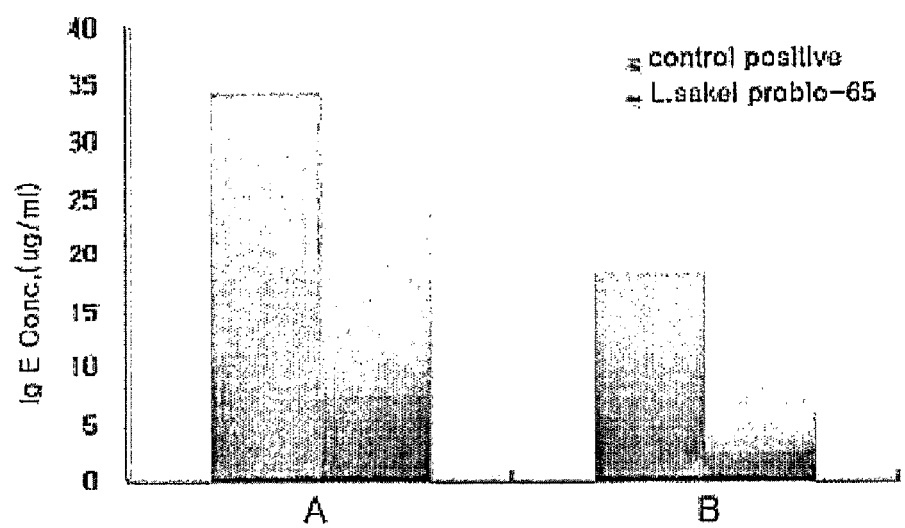
FIG. 1 is a graph showing the effect of *Lactobacillus sakei* Probio-65 on serum IgE concentrations of mice sensitized with DNCB to induce contact dermatitis.
Figure 2:
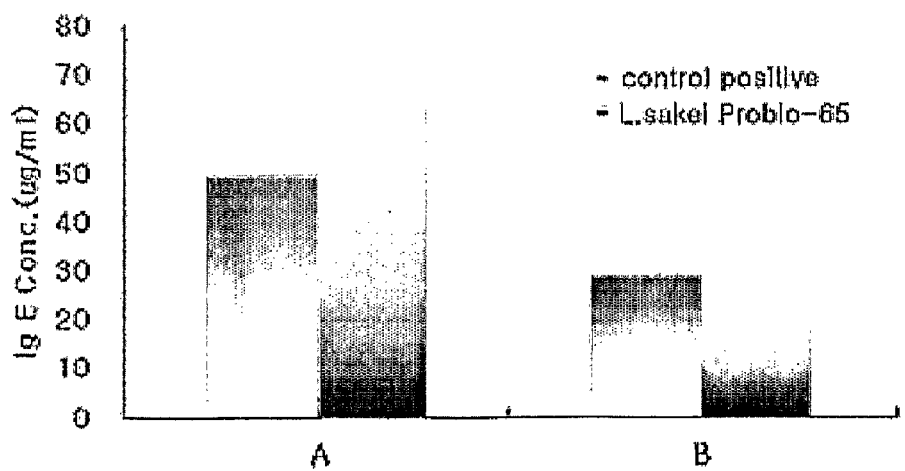
FIG. 2 is a graph showing the effect of *Lactobacillus sakei* Probio-65 on serum IgE concentrations of mice sensitized with TDI to induce contact dermatitis.
Figure 3:
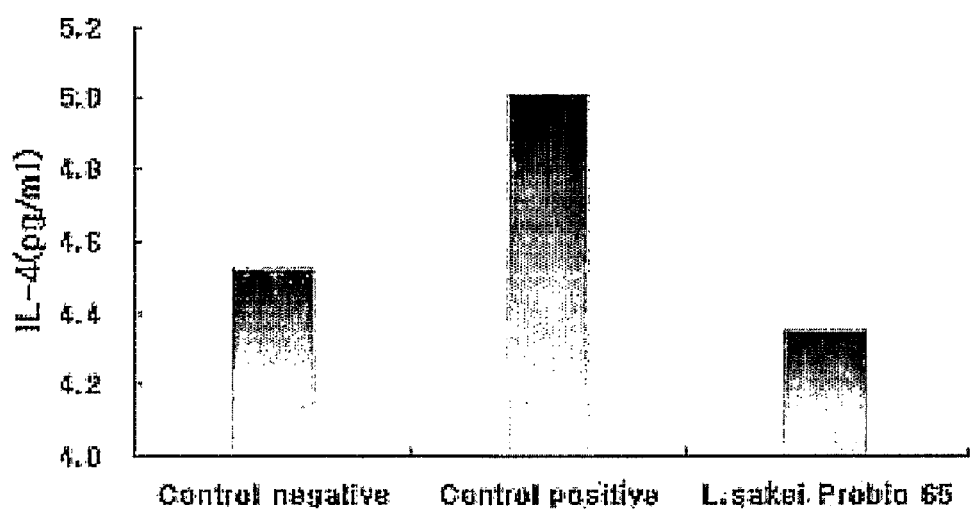
FIG. 3 is a graph showing the effect of *Lactobacillus sakei* Probio-65 on IL-4 concentrations of mice sensitized with DNCB to induce contact dermatitis.
Figure 4:
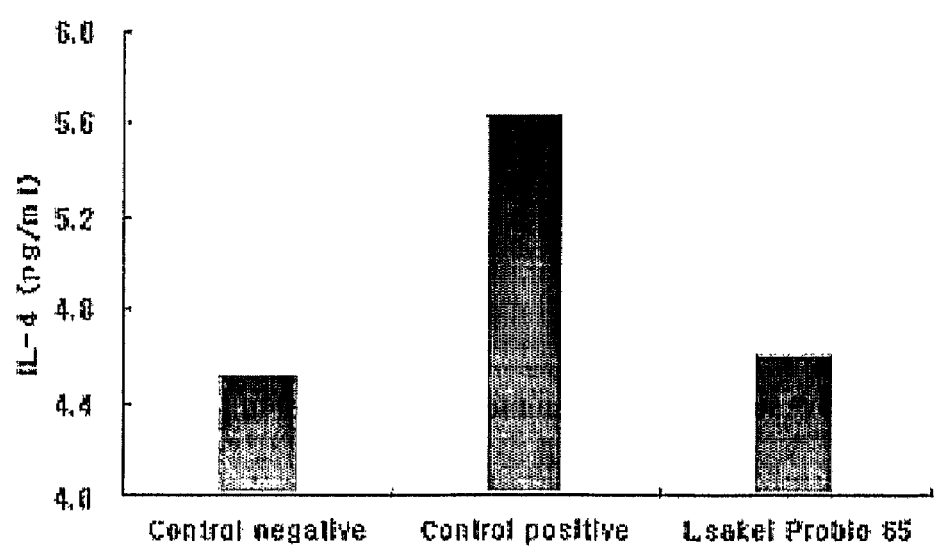
FIG. 4 is a graph showing the effect of *Lactobacillus sakei* Probio-65 on IL-4 concentrations of mice sensitized with TDI to induce contact dermatitis.
Figure 5:
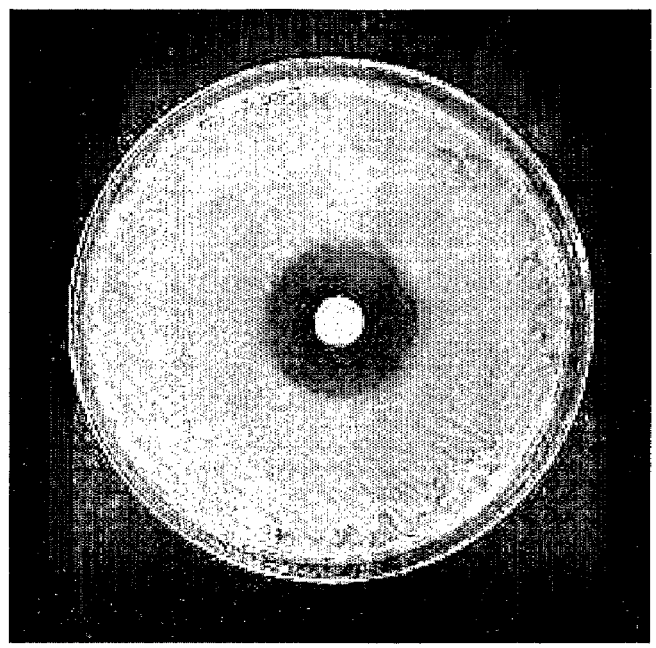
FIG. 5 is a photograph showing the growth inhibitory effect of *Lactobacillus sakei* Probio-65 on *Staphylococcus aureus*, wherein a clear zone was formed.

In one aspect, the present invention provides a novel microorganism belonging to the genus *Lactobacillus*. The *Lactobacillus* sp. strain according to the present invention is *Lactobacillus sakei* Probio-65, which has excellent properties of being acid-tolerant, being bile acid-tolerant, inhibiting the growth of harmful pathogenic microorganisms, especially, *Staphylococcus aureus*, which is a factor aggravating atopic disorders, regulating abnormal intestinal fermentation, and enhancing the immune system.

*Lactobacillus* species are widely distributed in nature, and anaerobically metabolize carbohydrates to produce lactic acid. Typically, it is known that when lactic acid bacteria such as *Lactobacillus* species are added directly or indirectly to food products, their metabolite, lactic acid, improves the storage stability, flavor, and texture of food products. Also, when lactic acid bacteria are ingested along with fermented food, they enter the intestine and adhere to intestinal epithelial cells, where they offer various beneficial effects, such as inhibiting and antagonizing pathogenic microorganisms, enhancing immune function, reducing the incidence of cancer, and reducing carcinogenic enzymes, to host animals. Thus, lactic acid bacteria, in both Western and Oriental countries, are used as auxiliary components in the processing of dairy products, meat products, pickled vegetables and various pickled and fermented seafoods, and, as well, they are used as probiotics. In order to use lactic acid bacteria as probiotics, the lactic acid bacteria should meet the following requirements: they should have resistance to gastric acid or bile acid so as to arrive in the intestine at a high density; they should adhere to intestinal epithelial cells or mucous membranes and settle therein; they should preferably secrete antimicrobial substances to inhibit harmful bacteria, thereby stabilizing the intestine and preventing harmful bacteria from settling in the intestine; and they should be safe for use in food products.

The present *Lactobacillus* sp. strain, *Lactobacillus sakei* Probio-65, is a novel microorganism meeting all of the aforementioned requirements.

The *Lactobacillus sakei* Probio-65 strain of the present invention, which is a novel probiotic microorganism, is able to adhere to intestinal cells and possesses the following probiotic properties.

First, the present microorganism has the ability to survive in an aerobic or anaerobic environment at various pH values. This property enables the present microorganism to adapt well to physiological and pathological conditions that vary in the gastrointestinal tract.

Second, the present microorganism has tolerance to gastric acid and bile acid, and possesses probiotic activity when lyophilized.

Third, the present microorganism has the ability to inhibit the growth of harmful pathogenic microorganisms. The harmful microorganisms include, but are not limited to, *E. coli* KCTC 2441, *Klebsiella pneumoniae* KCTC 2208, *Staphylococcus aureus* KCTC 1621, *Staphylococcus epidermidis* KCTC 1917, *Shigella flexneri* KCTC 2008, *Salmonella gallinarum*, *Enterobacter cloacea* KCTC 2361, *Salmonella typhimurium*, *Citrobacter freundii* KCTC 2006, and *Methylosinus trichosporium* KCTC 2591. In particular, the present microorganism inhibits the growth of *Staphylococcus aureus*, which is a major cause of the worsening of atopic dermatitis.

Fourth, the present microorganism has excellent resistance to antibiotics. Examples of such antibiotics include ampicillin, carbenicillin, clindamycin, doxycycline, erythromycin, gentamycin, kanamycin, lincomycin, minocyclin, neomycin, penicillin G, streptomycin, sulfisoxazole, and tetracycline.

Fifth, the present microorganism is safe to humans and has no side effects such as biological toxicity.

The *Lactobacillus* sp. strain according to the present invention was isolated and identified according to the following procedure. First, Kimchi juice (fermented) was serially diluted and incubated in a medium selecting for lactic acid bacteria so as to isolate only lactic acid bacteria. Micrococci and bacilli were selected and cultured in MRS medium. Finally, a microorganism inhibiting the proliferation of *Staphylococcus aureus*, which is a factor aggravating atopic dermatitis, was isolated.

The *Lactobacillus sakei* Probio-65 isolated from Kimchi according to the present invention has the following morphological, physical and biochemical characteristics. The *Lactobacillus sakei* Probio-65 is a Gram-positive bacterium, which grows under both aerobic and anaerobic conditions, does not form spores, is non-motile, and is a bacillus type. The optimal temperature of the strain ranges from 30° C. to 37° C. The present microorganism does not generate gas and indole, does not display lytic properties, and does not reduce nitric acid.

16S rDNA-based phylogenetic analysis resulted in the finding that the present microorganism has the 16S rDNA sequence of SEQ ID No. 1. The present microorganism, which belongs to the genus *Lactobacillus*, was identified as a strain showing the closest phylogenetic relationship with a standard strain of *Lactobacillus sakei*, with 99.6% of 16S rDNA sequence homology.

Based on the results, the present microorganism was identified as a novel strain of *Lactobacillus sakei*, *Lactobacillus sakei* Probio-65, and deposited at KCTC (Korean Collection for Type Cultures; Genetic Resources Center, KRIBB, 52, Oun-dong, Yusong-ku, Taejon, Korea) on Dec. 23, 2004, and assigned accession number KCTC 10755BP.

The present microorganism may be cultivated on a large scale according to an ordinary method for cultivating *Lactobacillus* species. A medium composed of a carbon source, a nitrogen source, vitamins and minerals may be use as a culture medium. Examples of culture media may include MRS broth (de Man-Rogosa-Sharp broth) and milk-supplemented broth. The microbial cultivation may be carried out under ordinary culture conditions of lactic acid bacteria, for example, at a temperature ranging from 15° C. to 45° C. for a period ranging from 10 hours to 40 hours. If desired, those skilled in the art may conduct centrifugation or filtration in order to remove the culture medium from the resulting culture and harvest cultured cells a concentrated state. The concentrated cell mass may be frozen or lyophilized according to an ordinary method to preserve the cells without loss in activity. Preferably, the present microorganism is mixed with glycerol and stored at −80° C., or is suspended in sterile 10% skim milk and lyophilized, so as to be stably preserved for a long period of time.

It will be apparent to those skilled in the art that the present microorganism may be improved or modified by ordinary physicochemical mutagenesis so as to have excellent stability or higher antimicrobial activity, while retaining the same activity.

In another aspect, the present invention provides a composition for inhibiting the growth of harmful pathogenic microorganisms, comprising *Lactobacillus sakei* Probio-65 or a culture thereof.

The term "Probiotics", as used herein, refers to a live microorganism or a culture thereof, which beneficially affects host animals including humans by improving their intestinal microbial balance in the gastrointestinal tract of host animals, and may further mean a microorganism or a culture thereof, which is capable of improving a microbial balance in vivo or in vitro as well as the gastrointestinal tract. The term "culture", as used herein, refers to a microorganism harvested from the culture fluid thereof, or a substance extracted from the culture fluid containing the microorganism using an extraction solvent. A microorganism may be harvested from the culture fluid thereof by centrifugation, organic solvent treatment, and the like. Useful active components may be extracted by sonicating cells or treating cells with a solvent, such as methanol and acetone, and concentrating the cell lysate.

In order to determine whether the *Lactobacillus sakei* Probio-65 of the present invention has growth inhibitory activity versus harmful pathogenic microorganisms, the present inventors examined the growth inhibitory effects of primarily isolated microorganisms against harmful microorganisms according to a cylinder plate method which is a modification of Kuroiwa's method (Kuroiwa et al., Journal of Infections, 64, 257, 1990) (Example 3). In this assay, the optimal temperature of *Lactobacillus sakei* Probio-65 for inhibiting harmful microorganisms preferably ranges from 30° C. to 37° C. The diameter of clear zones of growth inhibition, emerging after cultivation, was measured, and the primarily isolated strains were compared with each other for growth inhibitory activity against pathogenic microorganisms. Ten harmful microorganisms used in the antibiotic activity evaluation were obtained from the Korean Research Institute of Bioscience and Biotechnology (KRIBB), and were as follows: *E. coli* KCTC 2441, *Klebsiella pneumoniae* KCTC 2208, *Staphylococcus aureus* KCTC 1621, *Staphylococcus epidermidis* KCTC 1917, *Shigella flexneri* KCTC 2008, *Salmonella gallinarum*, *Enterobacter cloacea* KCTC 2361, *Salmonella typhimurium*, *Citrobacter freundii* KCTC 2006, and *Methylosinus trichosporium* KCTC 2591. The harmful microorganisms were individually cultured in nutrient broth (NB) at 37° C. for 18 hours. 0.1 ml of each culture fluid was smeared onto nutrient agar (NA) plates and air-dried, and a cylinder 8 mm in diameter was placed onto each plate. Separately, the primarily isolated microorganisms were individually cultured in MRS broth under an aerobic condition at 37° C. for 18 hours. In order to extract antimicrobial substances produced by the isolated microorganisms, each culture fluid of the isolated microorganisms was mixed with an equal 5 volume of pre-chilled acetone and allowed to react for 24 hours. The reaction mixtures were then centrifuged, and the supernatants were concentrated under pressure for use in the following evaluation of the antimicrobial activity of the microorganisms. Then, 30 µl of each concentrate was inoculated onto the 8-mm-diameter cylinder placed on the NA plate, followed by incubation at 37° C. for 24 hours. The diameter of formed clear zones of growth inhibition was measured and compared with a control. The strain showing the highest growth inhibitory activity versus harmful pathogenic microorganisms was selected and designated "Probio-65".

The *Lactobacillus sakei* Probio-65 strain of the present invention formed clear zones of growth inhibition against the harmful pathogenic microorganisms, and the diameter of the clear zones was as follows: 27 mm against *E. coli* KCTC 2441, 41 mm against *Klebsiella pneumoniae* KCTC 2208, 28 mm against *Staphylococcus aureus* KCTC 1621, 24 mm against *Staphylococcus epidermidis* KCTC 1917, 31 mm against *Salmonella gallinarum*, 28 mm against *Enterobacter cloacea* KCTC 2361, 28 mm against *Salmonella typhimurium*, 28 mm against *Citrobacter freundii* KCTC 2006, 26 mm against *Shigella flexneri* KCTC 2008, and 16 mm against *Methylosinus trichosporium* KCTC 2591 (Table 3).

In particular, the present microorganism, *Lactobacillus sakei* Probio-65, as described above, exhibited an excellent growth inhibitory effect on *Staphylococcus aureus*, which is known to be a factor aggravating atopic dermatitis, and is thus potentially useful in the preparation of a composition for preventing and treating atopic dermatitis.

In addition, the present *Lactobacillus sakei* Probio-65 strain was found to have antibiotic resistance, and thus, may be administered alone as a substitute for conventional antibiotics or in combination with conventional antibiotics to humans or animals in order to inhibit the growth of harmful intestinal microorganisms.

In detail, the *Lactobacillus sakei* Probio-65 strain was tested for antibiotic sensitivity against fourteen antibiotics according to a method described in Microbiology Procedures Handbook vol.1 (Henry D. Isenberg, ASM) and Korean Pat. Publication No. 91-4366. The results are given in Table 1, below.

TABLE 1

| Antibiotics | Conc. (µg) | Resistance (mm) | Diameter (mm) | Results |
|---|---|---|---|---|
| Ampicillin | 10 | <28 | 19 | R |
| Carbenicillin | 100 | <19 | 24 | S |
| Clindamycin | 2 | <14 | 20 | S |
| Doxycycline | 30 | <16 | 22 | S |
| Erythromycin | 15 | <21 | 19 | R |
| Gentamicin | 10 | <15 | 9 | R |
| Kanamycin | 30 | <18 | 0 | R |
| Lincomycin | 2 | <24 | 11 | R |
| Minocyclin | 30 | <14 | 26 | S |
| Neomycin | 30 | <12 | 9 | R |
| Penicillin G | 10 | <19 | 20 | RS |
| Streptomycin | 10 | <14 | 0 | R |
| Sulfisoxazole | 250 | <24 | 0 | R |
| Tetracycline | 30 | <19 | 20 | R |

(R; Resistant, S; Susceptible)

In a further aspect, the present invention provides a composition for preventing and treating abnormal fermentation in the intestine, comprising *Lactobacillus sakei* Probio-65 or a culture thereof.

The present composition has the effect of treating and improving symptoms caused by abnormal fermentation of intestinal bacterial flora. When the present microorganism is administered to humans and animals, it localizes and settles on the wall of the digestive tract of the intestine to prevent harmful bacteria from settling therein, and produces lactic acid, which lowers the intestinal pH, thereby inhibiting the proliferation of harmful bacteria. The present microorganism also produces bacteriocins and peroxides in order to inhibit the proliferation of pathogenic bacteria.

In yet another aspect, the present invention provides a composition for treating or preventing allergy-associated disorders, comprising *Lactobacillus sakei* Probio-65 or a culture thereof.

The present composition enhances immune function and, in particular, inhibits allergic disorders. The present inventors induces allergic contact dermatitis in mice using a contact allergen, 1-chloro 2,4-dinitrobenzene (DNCB), and a respiratory allergen, toluene d-isocyanate (TDI), which act through a mechanism similar to that of picryl chloride (1-chloro-2,4,6-trinitrobenzene), which serves as a hapten, and the present microorganism was evaluated for its therapeutic effects on the induced allergic contact dermatitis (Example 4). In mice sensitized with DNCB or TDI to induce contact dermatitis, serum IgE concentrations and IL-4 concentrations in splenocytes were measured to determine whether the present microorganism has the effect of reducing the IgE and IL-4 levels.

The above composition of the present invention may be formulated into various dosage forms and administered. For example, the composition may be prepared by mixing an effective amount of *Lactobacillus sakei* Probio-65 with a carrier commonly used in the pharmaceutical field. The effective amount of *Lactobacillus sakei* Probio-65 is preferably more than $10^7$ cells/g. Examples of carriers may include binders, lubricants, disintegrators, excipients, solubilizers, dispersing agents, stabilizers, suspending agents, colorants, and perfumes. The present composition may be formulated into tablets, troches, capsules, elixirs, suspensions, syrups, wafers, powders, granules, and ointments. The present composition may be administered orally and parenterally, i.e., by intravenous, intramuscular, subcutaneous, topical, sublingual, intranasal or intraperitoneal administration. Oral administration is preferred. The dosage of the present composition may be suitably determined depending on the in vivo absorption and inactivation rates and excretion rates of active ingredients, the patient's age, gender and health state, and the severity of the illness to be treated.

In still another aspect, the present invention provides a feed composition comprising *Lactobacillus sakei* Probio-65 or a culture thereof.

The feed composition of the present invention, which is useful as a substitute for conventional antibiotics, inhibits harmful microorganisms in the intestine and maintains stable intestinal flora, thereby maintaining animals in good states of health, and improving body weight gain and meat quality, increasing milk yield, and enhancing the immunity of livestock. The feed composition of the present invention may be prepared in the form of fermented feed, formula feed, pellets, and silage. The *Lactobacillus sakei* Probio-65 is contained in an effective amount of more than $10^7$ cells/g, and preferably more than $10^5$ cells/g, in the feed composition. Fermented feed may be prepared by adding several microorganism populations or enzymes to organic matter and fermenting the organic matter. Formula feed may be prepared by mixing several kinds of general feed with the *Lactobacillus sakei* of the present invention. Pellet feed may be prepared by applying heat and pressure to the formula feed in a pelletizer. Silage may be prepared by fermenting green forage plants using the lactic acid bacterium according to the present invention. Among these, the fermented feed, after being fermented, has a pH value of about 4.0, at which the proliferation of different kinds of harmful microorganisms is inhibited, and thus has improved stability for a prolonged period of time. The fermented feed also has enhanced feed preference because it contains plant proteins as well as proteins from lactic acid bacteria and yeasts. The fermented feed may be prepared by a wet fermentation method and a fermentation drying method. Wet fermented feed may be prepared by collecting and transporting organic matter such as food garbage, mixing the organic matter with an absorptive bulking agent for sterilization and water content control in a predetermined ratio, performing fermentation at 50° C. to 60° C. for 24 hrs or longer, and adjusting the water content to about 70%. Fermented dry feed may be prepared by adding suitable amounts of energy sources, proteins, fibrous materials and a microorganism to organic matter such as food waste, performing fermentation at about 60° C. for 24 hrs or longer, drying the fermented materials, and adjusting the water content to about 30% to 40%.

In still another aspect, the present invention provides a food (or heath functional food) composition comprising *Lactobacillus sakei* Probio-65 or a culture thereof.

Lactic acid bacteria are beneficial to humans because they produce lactic acid as an end product of sugar fermentation, thereby preventing food spoilage, and secrete antimicrobial substances such as bacteriocins, thereby inhibiting food-poisoning bacteria, and lower the intestinal pH of humans, thereby inhibiting the proliferation of spoilage bacteria in the intestine. Food products prepared by fermentation using lactic acid bacteria include cheese, butter milk, yogurt, and whey. Recently, functional yogurt prepared by lactic acid bacteria fermentation has been widely available. Also, lactic acid bacteria fermentation products are formulated into tablets, granules, and the like, and marketed as food compositions, medicaments, and the like, applicable as probiotics.

The food composition of the present invention, in addition to the present microorganism or a culture thereof, may be mixed with suitable carriers and excipients or auxiliary effective ingredients, and may be formulated into powders, granules, tablets, capsules or liquids (e.g., drinkable form). That is, the food composition of the present invention may be formulated into powders and granules by a known method, such as lyophilization, using standard carriers, and may also be formulated into tablets and capsules using ordinary tableting and capsulating methods. Also, the food composition of the present invention may be enteric-coated using a known method so as to pass through gastrointestinal tracts to arrive at the small intestine and rapidly release active ingredients into the intestine. Suitable carriers, excipients and diluents for use in the formulation of the food composition of the present invention include lactose, dextrose, sucrose, sorbitol, mannitol, starch, gum acacia, calcium phosphate, alginate, gum tragacanth, gelatin, calcium silicate, microcrystalline cellulose, polyvinylpyrrolidone, cellulose, water, syrup, methylcellulose, methyl- and propyl-hydroxybenzoate, talc, magnesium stearate and mineral oils. For commercialization, the food composition of the present invention may further include lubricants, wetting agents, emulsifying agents and suspending agents, antiseptics, sweeteners, or perfumes.

In still another aspect, the present invention provides a cosmetic composition comprising a culture of *Lactobacillus sakei* Probio-65.

Typically, it is well known that when milk fermented with lactic acid bacteria is applied to the skin, it makes the skin white and prevents the skin from drying. Human skin cells contain natural moisturizing factors (e.g., amino acids, sodium lactate, PCA-sodium, urea, etc.), which regulate the moisture of the skin. Such natural moisturizing factors regulate the moisture of the skin to be suitable (15% to 25% moisturized) and also control the pH of the skin. When such natural moisturizing factors are insufficient in the skin, the skin cannot maintain normal moisture states in dry air or in a severely aged state. Recently, fermentation fluids of lactic acid bacteria have been frequently used in liquid cosmetics having nutritional and moisturizing effects on the skin because they are composed of almost the same components as the natural moisturizing factors of the skin. This cosmetic use is based on the fact that the nutritional and moisturizing effects of the fermentation fluids of lactic acid bacteria result from lactic acid, lactose, proteospeptone, and other components. Thus, the culture of the present microorganism, *Lactobacillus sakei* Probio-65, may be used in the preparation of cosmetics having excellent nutritional and moisturizing effects.

In a preferred aspect, the pharmaceutical, feed, food and cosmetic compositions comprising *Lactobacillus sakei* Probio-65 or a culture thereof according to the present invention, in addition to *Lactobacillus sakei* Probio-65, may include two or more other beneficial microorganisms.

Preferably, the other microorganisms capable of being used along with the present microorganism are those which are suitable for intake by humans or animals and have probiotic activity, thereby inhibiting harmful pathogenic microorganisms or improving the intestinal microbial balance in the intestine of mammals when ingested. Examples of such probiotic microorganisms include yeasts, such as *Saccharomyces, Candida, Pichia*, and *Torulopsis;* fungi, such as *Aspergillus, Rhizopus, Mucor*, and *Penicillium;* and bacteria, such as *Lactobacillus, Bifidobacterium, Clostridium, Leuconostoc, Bacteroides, Staphylococcus, Lactococcus, Bacillus, Streptococcus, Fusobacterium, Propionibacterium, Enterococcus, Pediococcus*, and *Micrococcus*. Detailed examples of suitable probiotic microorganisms include *Saccharomyces cereviseae, Bacillus coagulans, Bacillus licheniformis, Bacillus subtilis, Bifidobacterium bifidum, Bifidobacterium infantis, Bifidobacterium longum, Lactobacillus sakei, Enterococcus faecalis, Lactobacillus acidophilus, Lactobacillus alimentarius, Lactobacillus casei, Lactobacillus curvatus, Lactobacillus delbruckii, Lactobacillus johnsonii, Lactobacillus farciminus, Lactobacillus gasseri, Lactobacillus helveticus, Lactobacillus rhamnosus, Lactobacillus reuteri, Lactobacillus sake, Lactococcus lactis, Micrococcus varians, Pediococcus acidilactici*, and *Staphylococcus xylosus*.

A better understanding of the present invention may be obtained through the following examples which are set forth to illustrate, but are not to be construed as the limit of the present invention.

EXAMPLE 1

Isolation of *Lactobacillus* sp. Strains

Figure 6:
FIG. 6 is an electron microscopic observation of *Lactobacillus sakei* Probio-65.

Home-made Kimchi juice (fermented) was diluted, smeared onto BCP solid medium (Eiken Chemical, Japan), and cultured at 37° C. for 48 hrs. After emerged colonies were microscopically observed, a total of 480 micrococci and bacilli were selected, cultured in MRS medium (Difco), and stored at −80° C. Finally, a microorganism inhibiting the proliferation of *Staphylococcus aureus* KCTC1621, which is a factor aggravating atopic diseases, was selected and designated *Lactobacillus sakei* Probio-65 (FIG. 6).

EXAMPLE 2

Identification of the Isolated *Lactobacillus sakei* Probio-65 Strain

The Probio-65 strain isolated in Example 1 was cultured in MRS medium (Difco) at 37° C. In order to identify the Probio-65 strain, the morphological and physiological characteristics of the Probio-65 strain were determined using a method described in the literature: Yoon et al., *Int. J. Syst. Bacteriol.*, 47, 904, 1997 using API 32A and API CHL systems (BioMerieux). The nucleotide sequence of 16S rDNA gene was determined and analyzed using a method described in Yoon et al., *Int. J. Syst. Bacteriol.*, 47, 933, 1997.

The Probio-65 strain was found to be a Gram-positive bacterium. The bacterial strain grew under both aerobic and anaerobic conditions, did not form spores, was non-motile, and was a bacillus type. The optimal temperature for the growth of the strain ranged from 30° C. to 37° C. The Probio-65 strain did not generate gas and indole, did not display lytic properties, and did not reduce nitric acid. Also, the bacterial strain showed resistance to 0.5% bile acid.

TABLE 2

The morphological, physiological and growth characteristics of *L. sakei* Probio-65

| Characteristics | Results |
| --- | --- |
| Gram staining | + |
| Anaerobic growth | + |
| Aerobic growth | + |
| Spore formation | − |
| Mobility | − |
| Shape | Bacillus-type |
| Gas generation | − |
| Indole generation | − |
| Hemolysis | − |
| Nitric acid reduction | − |

EXAMPLE 3

Evaluation of the Inhibitory Effects of the Isolated Microorganism on Harmful Microorganisms The primarily isolated microorganisms were evaluated for growth inhibitory activity versus harmful pathogenic microorganisms using a method described by Kuroiwa et al. (Kuroiwa et al., Journal of Infections, 64, 257, 1990). In this antibiotic activity evaluation, ten microbial strains were used: *E. coli* KCTC 2441, *Klebsiella pneumoniae* KCTC 2208, *Staphylococcus aureus* KCTC 1621, *Staphylococcus epidermidis* KCTC 1917, *Shigella flexneri* KCTC 2008, *Salmonella gallinarum*, *Enterobacter cloacea* KCTC 2361, *Salmonella typhimurium*, *Citrobacter freundii* KCTC 2006, and *Methylosinus trichosporium* KCTC 2591.

The harmful pathogenic microorganisms were individually cultured in nutrient broth (NB) at 37° C. for 18 hrs. 0.1 ml of each culture fluid was smeared onto nutrient agar (NA) plates and air-dried, and a cylinder 8 mm in diameter was placed onto each plate. Separately, the primarily isolated microorganisms were individually cultured in MRS broth under an aerobic condition at 37° C. for 18 hrs. In order to extract antimicrobial substances produced by the isolated microorganisms, the fluid of each culture of the isolated microorganisms was mixed with an equal volume of acetone pre-chilled to 4° C., and was allowed to react for 24 hours. The reaction mixtures were then centrifuged, and the supernatants were concentrated under pressure for use in the following evaluation of the antimicrobial activity of the microorganisms. Then, 30 µl of each concentrate was inoculated onto the 8-mm-diameter cylinder placed on the NA plate, followed by incubation at 37° C. for 24 hours. The diameter of formed clear zones of growth inhibition was measured and compared with a control. The inhibitory activity of the finally isolated microorganism, *L. sakei* Probio-65, versus harmful pathogenic microorganisms is summarized in Table 3, below.

TABLE 3

The inhibitory activity of *L. sakei* Probio-65 versus harmful pathogenic microorganisms

| Harmful pathogenic microorganisms | Clear zones (mm) |
| --- | --- |
| *E. coli* KCTC 2441 | 27 |
| *Klebsiella pneumoniae* KCTC 2208 | 41 |
| *Staphylococcus aureus* KCTC 1621 | 28 |
| *Staphylococcus epidermidis* KCTC 1917 | 24 |
| *Shigella flexneri* KCTC 2008 | 26 |
| *Salmonella gallinarum*) | 31 |
| *Enterobacter cloacea* KCTC 2361 | 28 |
| *Salmonella typhimurium* | 28 |
| *Citrobacter freundii* KCTC 2006 | 28 |
| *Methylosinus trichosporium* KCTC 2591 | 16 |

As shown in Table 3, the *Lactobacillus sakei* Probio-65 strain was found to have excellent growth inhibitory activity versus the ten tested harmful pathogenic microorganisms. These results indicate that the present strain is a very useful microorganism.

EXAMPLE 4

Evaluation of the Therapeutic Effects of the Isolated Microorganism on Contact Dermatitis Induced By Skin Sensitization Female 4-week-old CD-1 (ICR) mice were purchased from Orientbio Co. Ltd., Korea, each test group consisting of six mice. The test was repeated three times. Mice were sensitized with an allergen, 1-chloro 2,4-dinitrobenzene (DNCB) or toluene d-isocyanate (TDI), to induce contact dermatitis. On Day 7, a sensory evaluation was carried out, and contact dermatitis of a score of 10 or higher was induced in all mice. DNCB induced severe erythema, edema and escoriation, and erosion, and TDI induced conspicuous pruritus and dry skin, and lichenification. When the sensitized mice were treated with the isolated microorganism, *L. sakei* Probio-65, no edema was observed in both cases, and thus, mice had a score of 12 upon a sensory evaluation. Hair did not grow on the back of mice sensitized with the allergens. This was considered to result from skin keratinization due to the induced dermatitis.

EXAMPLE 4-1

The Effect of Reducing Serum IgE Levels of Skin-sensitized Mice

The isolated *Lactobacillus sakei* Probio-65 strain was evaluated for immunoenhancing activity by measuring serum IgE levels in blood samples from sensitized mice.

Before being sensitized with an allergen, all five test groups, negative control, positive control (+DNCB), positive control (+TDI), Probio-65 treatment group (+DNCB), and Probio-65 treatment group (+TDI), displayed IgE levels of lower than 0.1 µg/ml, which was lower than the typical level of 0.2 µg/ml. Immediately after being sensitized with DNCB, compared to negative control mice, positive control mice displayed 1175-fold higher IgE levels, and mice treated with *L. sakei* Probio-65 displayed 1092-fold higher IgE levels. After being sensitized with an allergen, mice (Probio-65 treatment groups) ingested *L. sakei* Probio-65 along with feed, and also, an ointment, which was prepared by formulating immunoactive substances extracted from *L. sakei* Probio-65 into a cream form, was applied to skin lesions twice per day. After a test period, serum samples were prepared and assessed for IgE levels. Positive control groups and Probio-65 treatment groups all displayed a reduction in serum IgE levels. Positive control groups showed a 46.4% reduction from 34.079 μg/ml to 18.266 μg/ml. In contrast, *L. sakei* Probio-65 treatment groups displayed a 70.75% reduction from 31.687 μg/ml to 9.266 μg/ml. These results indicate that *L. sakei* Probio-65 had the effect of reducing serum IgE levels.

TABLE 4

The serum IgE level-reducing effect of *L. sakei* Probio-65 upon skin sensitization with DNCB

| | A | B | C | D.R. (%) |
|---|---|---|---|---|
| Control (−) | 0.065 | 0.029 | 0.043 | |
| Control (+) | 0.018 | 34.079 ± 10.05 | 18.266 ± 2.97 | 46.4 |
| Probio-65 | 0.039 | 31.687 ± 15.78 | 9.266 ± 4.29 | 70.75 |

Unit: μg/ml
A: before allergen sensitization
B: between allergen sensitization and ointment application
C: after ointment application
D.R.: decreased rate (%)

TABLE 5

The serum IgE level-reducing effect of *L. sakei* Probio-65 upon skin sensitization with TDI

| | A | B | C | D.R. (%) |
|---|---|---|---|---|
| Control (−) | 0.065 | 0.029 | 0.043 | |
| Control (+) | 0.037 | 49.1 ± 20.17 | 28.689 ± 6.29 | 41.57 |
| Probio-65 | 0.045 | 67.5 ± 26.27 | 24.895 ± 4.32 | 63.12 |

Unit: μg/ml
A: before allergen sensitization
B: between allergen sensitization and ointment application
C: after ointment application
D.R.: decreased rate (%)

EXAMPLE 4-2

The Effect of Reducing IL-4 Levels in Splenocytes of Skin-sensitized Mice

Sensitized mice were sacrificed by cervical dislocation, and spleens were aseptically excised from mice. Fat and connective tissue were removed from the excised spleens. Single cell suspensions were prepared and centrifuged. After supernatants were discarded, erythrocytes were disrupted. Splenocytes thus isolated were cultured, and culture supernatants were recovered and assessed for interleukin-4 (IL-4) levels in order to determine the immunological effect of *L. sakei* Probio-65.

The culture supernatants were obtained from the culture of splenocytes at a density of $1 \times 10^6$ cells/ml. A negative control showed an IL-4 level of 4.523 pg/ml. Positive controls sensitized with DNCB and TDI displayed IL-4 levels of 5.007 pg/ml and 5.643 pg/ml, respectively, which were increased by 0.5 to 1.0 pg/ml compared to the negative control.

When allergen-sensitized mice were treated with a culture of *L. sakei* Probio-65 and the ointment, they exhibited IL-4 levels of 4.352 pg/ml when sensitized with DNCB and 4.614 pg/ml when sensitized with TDI. These IL-4 levels were similar to those of the negative control.

INDUSTRIAL APPLICABILITY

The novel *Lactobacillus sakei* Probio-65 strain according to the present invention has acid tolerance and bile acid tolerance, inhibits the growth of harmful pathogenic microorganisms, and has immunoenhancing activity. In particular, the present strain has an excellent growth inhibitory effect on *Staphylococcus aureus*, which is a factor aggravating atopic dermatitis. Thus, the present strain is useful for preventing and treating atopic dermatitis and allergy-related disorders. Also, since the present strain stabilizes intestinal microflora, it is useful for preventing and treating abnormal intestinal fermentation. The present microorganism or a culture thereof is useful in pharmaceutical, feed, food, and cosmetic compositions.

The invention claimed is:

1. An isolated, *Lactobacillus sakei* Probio-65 (KCTC 10755BP).

* * * * *

UNITED STATES PATENT AND TRADEMARK OFFICE
CERTIFICATE OF CORRECTION

PATENT NO. : 8,034,606 B2
APPLICATION NO. : 11/883398
DATED : October 11, 2011
INVENTOR(S) : Yong Ha Park et al.

It is certified that error appears in the above-identified patent and that said Letters Patent is hereby corrected as shown below:

On the Title Page:
Item (54) reads:

"(54) ACID TOLERANT LACTOBACILLUS SAKEI PROBIO-65 WITH THE ABILITY OF GROWTH SUPPRESSION OF PATHOGENIC MICROORGANISMS AND THE ANTI-ALLERGIC EFFECT"

However, it should read:

"(54) NOVEL ACID TOLERANT LACTOBACILLUS SAKEI PROBIO-65 WITH THE ABILITY OF GROWTH SUPPRESSION OF PATHOGENIC MICROORGANISMS AND THE ANTI-ALLERGIC EFFECT"

On the title page:
Item (57) ABSTRACT:
Reads:

"Disclosed are a novel tactic acid bacterium, Lactobacillus sakei Probio-65, and the use thereof. The L. sakei Probio-65 strain has acid tolerance, bile acid tolerance and antibiotic resistance, inhibits the growth of harmful pathogenic microorganisms in the body and the intestine of animals, and has immunuenhancing activity. In particular, the novel strain inhibits the growth of Staphylocccus aureus, which is known to be a factor aggravating atopic dermatitis. Thus, the novel strain is useful for preventing or treating atopic dermatitis and allergy-related disorders. Also, the novel strain stabilizes intestinal microflors by inhibiting the abnormal proliferation of harmful microorganisms in the intestine. The L. sakei Probio-65 strain or a culture thereof is useful in pharmaceutical, feed, food, and cosmetic compositions."

However, it should read:

Signed and Sealed this
Twenty-ninth Day of November, 2011

David J. Kappos
*Director of the United States Patent and Trademark Office*

CERTIFICATE OF CORRECTION (continued)
U.S. Pat. No. 8,034,606 B2

"(57) ABSTRACT

Disclosed are a novel --lactic-- acid bacterium, Lactobacillus sakei Probio-65, and the use thereof. The L. sakei Probio-65 strain has acid tolerance, bile acid tolerance and antibiotic resistance, inhibits the growth of harmful pathogenic microorganisms in the body and the intestine of animals, and has --immunoenhancing-- activity. In particular, the novel strain inhibits the growth of --Staphylococcus-- aureus, which is known to be a factor aggravating atopic dermatitis. Thus, the novel strain is useful for preventing or treating atopic dermatitis and allergy-related disorders. Also, the novel strain stabilizes intestinal --microflora-- by inhibiting the abnormal proliferation of harmful microorganisms in the intestine. The L. sakei Probio-65 strain or a culture thereof is useful in pharmaceutical, feed, food, and cosmetic compositions."

In the claims:
Column 15, Lines 44-45, Claim 1, reads:

"An isolated, *Lactobacillus sakei* Probio-65 (KCTC 10755BP)."

However, it should read:

"An isolated *Lactobacillus sakei* Probio-65 (KCTC 10755BP)."

UNITED STATES PATENT AND TRADEMARK OFFICE
CERTIFICATE OF CORRECTION

PATENT NO.          : 8,034,606 B2
APPLICATION NO.     : 11/883398
DATED               : October 11, 2011
INVENTOR(S)         : Yong Ha Park et al.

Page 1 of 1

It is certified that error appears in the above-identified patent and that said Letters Patent is hereby corrected as shown below:

Title Page,
Item [54], Title, the word "NOVEL" should be deleted and title is reinstated to read
--ACID TOLERANT LACTOBACILLUS SAKEI PROBIO-65 WITH THE ABILITY OF GROWTH SUPPRESSION OF PATHOGENIC MICROORGANISMS AND THE ANTI-ALLERGIC EFFECT--.

Signed and Sealed this
Third Day of January, 2012

David J. Kappos
*Director of the United States Patent and Trademark Office*

SEQUENCE LISTING

```
<160> NUMBER OF SEQ ID NOS: 1

<210> SEQ ID NO 1
<211> LENGTH: 1487
<212> TYPE: DNA
<213> ORGANISM: Lactobacillus Sakei Probio-65
<220> FEATURE:
<221> NAME/KEY: rRNA
<222> LOCATION: (1)..(1487)
<223> OTHER INFORMATION: Sequence of 16S rRNA
<220> FEATURE:
<221> NAME/KEY: misc_feature
<222> LOCATION: (787)..(787)
<223> OTHER INFORMATION: n is a, c, g, or t

<400> SEQUENCE: 1
gctggcggcg tgcctaatac atgcaagtcg aacgcactct cgtttagatt gaaggagctt      60
```

```
gctcctgatt gataaacatt tgagtgagtg gcggacgggt gagtaacacg tgggtaacct      120
gccctaaagt gggggataac atttggaaac agatgctaat accgcataaa acctaacacc      180
gcatggtgta gggttgaaag atggtttcgg ctatcacttt aggatggacc cgcggtgcat      240
tagttagttg gtgaggtaaa ggctcaccaa gaccgtgatg catagccgac ctgagagggt      300
aatcggccac actgggactg agacacggcc cagactccta cgggaggcag cagtagggaa      360
tcttccacaa tggacgaaag tctgatggag caacgccgcg tgagtgaaga aggttttcgg      420
atcgtaaaac tctgttgttg gagaagaatg tatctgatag taactgatca ggtagtgacg      480
gtatccaacc agaaagccac ggctaactac gtgccagcag ccgcggtaat acgtaggtgg      540
caagcgttgt ccggatttat tgggcgtaaa gcgagcgcag gcggtttctt aagtctgatg      600
tgaaagcctt cggctcaacc gaagaagtgc atcggaaact gggaaacttg agtgcagaag      660
aggacagtgg aactccatgt gtagcggtga aatgcgtaga tatatggaag aacaccagtg      720
gcgaaggcgc tgtctggtc tgtaactgac gctgaggctc gaaagcatgg gtagcaaaca      780
ggattanata ccctggtagt ccatgccgta aacgatgagt gctaggtgtt ggagggtttc      840
cgcccttcag tgccgcagct aacgcattaa gcactccgcc tggggagtac gaccgcaagg      900
ttgaaactca aaggaattga cgggggcccg cacaagcggt ggagcatgtg gtttaattcg      960
aagcaacgcg aagaaccttta ccaggtcttg acatcctttg accactctag agatagagct     1020
ttcccttcgg ggacaaagtg acaggtggtg catggttgtc gtcagctcgt gtcgtgagat     1080
gttgggttaa gtcccgcaac gagcgcaacc cttattacta gttgccagca tttagttggg     1140
cactctagtg agactgccgg tgacaaaccg gaggaaggtg gggacgacgt caaatcatca     1200
tgccccttat gacctgggct acacacgtgc tacaatggat ggtacaacga gttgcgagac     1260
cgcgaggttt agctaatctc ttaaaaccat tctcagttcg gattgtaggc tgcaactcgc     1320
ctacatgaag ccggaatcgc tagtaatcgc ggatcagcat gccgcggtga atacgttccc     1380
gggccttgta cacaccgccc gtcacaccat gagagtttgt aacacccaaa gccggtgagg     1440
taacccttcg gggagccagc cgtctaaggt gggacagatg attaggg                   1487
```